(12) United States Patent
Butler et al.

(10) Patent No.: US 7,951,151 B2
(45) Date of Patent: May 31, 2011

(54) STRUCTURE FOR JOINING AND RETAINING MULTI-PART ORTHOPEDIC IMPLANTS

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 620 days.

(21) Appl. No.: 11/709,022

(22) Filed: Feb. 21, 2007

(65) Prior Publication Data

US 2007/0233117 A1    Oct. 4, 2007

Related U.S. Application Data

(60) Provisional application No. 60/775,103, filed on Feb. 21, 2006.

(51) Int. Cl.
*A61B 17/80* (2006.01)
(52) U.S. Cl. .................... 606/71; 606/280; 606/282
(58) Field of Classification Search .................. 606/280, 606/273, 69, 71, 282; 403/292, 297, 298
See application file for complete search history.

(56) References Cited

U.S. PATENT DOCUMENTS

| | | | |
|---|---|---|---|
| 2,401,856 | A | 6/1946 | Brock |
| 3,741,205 | A | 6/1973 | Markolf et al. |
| 4,388,921 | A | 6/1983 | Sutter et al. |
| 4,794,918 | A | 1/1989 | Wolter |
| 4,808,185 | A | 2/1989 | Penenberg et al. |
| 5,364,399 | A | 11/1994 | Lowery et al. |
| 5,534,027 | A | 7/1996 | Hodorek |
| 5,607,426 | A | 3/1997 | Ralph et al. |
| 5,616,142 | A | 4/1997 | Yuan et al. |
| 5,803,277 | A * | 9/1998 | Alvarez-Momoitio ....... 211/188 |
| 5,951,558 | A | 9/1999 | Fiz |
| 6,139,550 | A | 10/2000 | Michelson |

(Continued)

FOREIGN PATENT DOCUMENTS

CH           674927 A5       8/1990

(Continued)

OTHER PUBLICATIONS

WO 2007/098188 A3. International Search Report relating to International Application No. PCT/07/04482, date of mailing of the International Search Report, Dec. 3, 2007 (3 pgs.).

(Continued)

*Primary Examiner* — Thomas C Barrett
*Assistant Examiner* — Nicholas Woodall
(74) *Attorney, Agent, or Firm* — Foley & Lardner LLP (57) ABSTRACT

An orthopedic implant structure is provided for joining and retaining components of a multi-part orthopedic device. The orthopedic implant joining and retaining structure may be embodied in two or more components of the multi-part orthopedic device. In one form, the multi-part orthopedic implant structure is a resilient snap structure such as a resilient flange in one part and a channel structure formed in another part of an orthopedic implant. A channel of the channel structure may have a cavity formed at a rear of the channel that accepts a configured lip formed on an end of the resilient flange. According to another embodiment, the retaining structure includes resilient snap flanges formed on an interconnection component of the multi-part orthopedic implant. A corresponding bore in another part of the multi-part orthopedic implant receives the interconnection component.

15 Claims, 10 Drawing Sheets

U.S. PATENT DOCUMENTS

| | | | |
|---|---|---|---|
| 6,152,927 | A | 11/2000 | Farris et al. |
| 6,193,721 | B1 | 2/2001 | Michelson |
| 6,224,602 | B1 | 5/2001 | Hayes |
| 6,228,085 | B1 | 5/2001 | Theken et al. |
| 6,235,034 | B1 | 5/2001 | Bray |
| 6,258,089 | B1 | 7/2001 | Campbell et al. |
| 6,273,889 | B1 | 8/2001 | Richelsoph |
| 6,306,136 | B1 | 10/2001 | Baccelli |
| 6,364,881 | B1 | 4/2002 | Apgar et al. |
| 6,398,783 | B1 | 6/2002 | Michelson |
| 6,402,756 | B1 | 6/2002 | Ralph et al. |
| 6,413,259 | B1 | 7/2002 | Lyons et al. |
| 6,428,542 | B1 | 8/2002 | Michelson |
| 6,454,769 | B2 | 9/2002 | Wagner et al. |
| 6,503,250 | B2 | 1/2003 | Paul |
| 6,533,786 | B1 | 3/2003 | Needham et al. |
| 6,599,290 | B2 | 7/2003 | Bailey et al. |
| 6,602,257 | B1 | 8/2003 | Thramann |
| 6,620,163 | B1 | 9/2003 | Michelson |
| 6,669,700 | B1 | 12/2003 | Farris et al. |
| 6,695,846 | B2 | 2/2004 | Richelsoph et al. |
| 6,854,919 | B2 * | 2/2005 | Neumann et al. ............ 403/326 |
| 6,872,210 | B2 | 3/2005 | Hearn |
| 6,974,460 | B2 | 12/2005 | Carbone et al. |
| 7,318,825 | B2 | 1/2008 | Butler et al. |
| 7,479,143 | B2 * | 1/2009 | Suh et al. ....................... 606/71 |
| 2001/0041894 | A1 | 11/2001 | Campbell et al. |
| 2002/0045896 | A1 | 4/2002 | Michelson |
| 2002/0045899 | A1 | 4/2002 | Errico et al. |
| 2002/0111630 | A1 | 8/2002 | Ralph et al. |
| 2002/0120273 | A1 | 8/2002 | Needham et al. |
| 2002/0128655 | A1 | 9/2002 | Michelson |
| 2002/0143336 | A1 | 10/2002 | Hearn |
| 2002/0147450 | A1 | 10/2002 | LeHuec et al. |
| 2002/0151899 | A1 | 10/2002 | Bailey et al. |
| 2002/0183754 | A1 | 12/2002 | Michelson |
| 2002/0183755 | A1 | 12/2002 | Michelson |
| 2002/0183756 | A1 | 12/2002 | Michelson |
| 2002/0183757 | A1 | 12/2002 | Michelson |
| 2002/0188296 | A1 | 12/2002 | Michelson |
| 2003/0023242 | A1 | 1/2003 | Harrington, Jr. |
| 2003/0040749 | A1 | 2/2003 | Grabowski et al. |
| 2003/0060828 | A1 | 3/2003 | Michelson |
| 2003/0083658 | A1 | 5/2003 | Hawkes et al. |
| 2003/0105462 | A1 | 6/2003 | Haider |
| 2004/0034356 | A1 | 2/2004 | LeHuec et al. |
| 2004/0068319 | A1 | 4/2004 | Cordaro |
| 2004/0087951 | A1 | 5/2004 | Khalili |
| 2004/0102773 | A1 | 5/2004 | Morrison et al. |
| 2004/0106924 | A1 | 6/2004 | Ralph et al. |
| 2004/0122426 | A1 | 6/2004 | Michelson |
| 2004/0127896 | A1 | 7/2004 | Lombardo et al. |
| 2004/0127897 | A1 | 7/2004 | Freid et al. |
| 2004/0127899 | A1 | 7/2004 | Konieczynski et al. |
| 2004/0181226 | A1 | 9/2004 | Michelson |
| 2004/0181229 | A1 | 9/2004 | Michelson |
| 2004/0186476 | A1 | 9/2004 | Michelson |
| 2004/0204712 | A1 | 10/2004 | Kolb et al. |
| 2004/0220571 | A1 | 11/2004 | Assaker et al. |
| 2004/0220572 | A1 | 11/2004 | Michelson |
| 2004/0236335 | A1 | 11/2004 | Michelson |
| 2005/0004574 | A1 | 1/2005 | Muckter |
| 2005/0027297 | A1 | 2/2005 | Michelson |
| 2005/0027298 | A1 | 2/2005 | Michelson |
| 2005/0033298 | A1 | 2/2005 | Hawkes et al. |
| 2005/0043732 | A1 | 2/2005 | Dalton |
| 2005/0059971 | A1 | 3/2005 | Michelson |
| 2005/0075699 | A1 | 4/2005 | Olson et al. |
| 2005/0116683 | A1 * | 6/2005 | Cheng et al. ................. 320/108 |
| 2005/0137597 | A1 | 6/2005 | Butler et al. |
| 2005/0149026 | A1 | 7/2005 | Butler et al. |
| 2005/0216010 | A1 | 9/2005 | Michelson |
| 2006/0116683 | A1 * | 6/2006 | Barrall et al. ................... 606/71 |
| 2006/0224241 | A1 | 10/2006 | Butler et al. |
| 2006/0235398 | A1 * | 10/2006 | Farris et al. ..................... 606/69 |
| 2007/0118122 | A1 | 5/2007 | Butler et al. |
| 2007/0233117 | A1 | 10/2007 | Butler et al. |
| 2008/0114361 | A1 | 5/2008 | Butler et al. |
| 2008/0208263 | A1 | 8/2008 | Butler et al. |

FOREIGN PATENT DOCUMENTS

| | | |
|---|---|---|
| DE | 29 33 141 A1 | 4/1980 |
| EP | 0 179 695 A1 | 4/1986 |
| EP | 0 313 762 A1 | 5/1989 |
| FR | 2 651 996 A3 | 3/1991 |
| WO | WO 91/03994 A1 | 4/1991 |
| WO | WO 95/30389 A1 | 11/1995 |
| WO | WO 96/03096 A1 | 2/1996 |
| WO | WO 96/23457 A1 | 8/1996 |
| WO | WO 2004/017837 A2 | 3/2004 |
| WO | WO 2005/062900 A2 | 7/2005 |

OTHER PUBLICATIONS

PCT Written Opinion of the International Searching Authority, relating to International Application No. PCT/US07/04482, date of completion of the Opinion, Oct. 26, 2007 (4 pgs.).

WO 2005/062902 A3, International Search Report relating to International Application No. PCT/US04/43172, date of mailing of the International Search Report, Nov. 1, 2005 (4 pgs.).

* cited by examiner

STRUCTURE FOR JOINING AND RETAINING MULTI-PART ORTHOPEDIC IMPLANTS

RELATED APPLICATIONS

This patent application claims the benefit of and/or priority to U.S. Provisional Patent Application No. 60/775,103 filed Feb. 21, 2006, entitled "Retaining Structure For Multi-Part Orthopedic Devices" the entire contents of which is specifically incorporated herein by reference.

FIELD OF THE INVENTION

The present invention relates to orthopedic devices and components and, more particularly, to a structure for joining and retaining parts of multi-part orthopedic devices.

BACKGROUND OF THE INVENTION

Orthopedic treatment for the correction of skeletal problems due to trauma, injury, disease, deformity or the like can include orthopedic surgery for implanting one or more orthopedic devices. Orthopedic surgery is now commonly used to implant artificial joints, mend bones and correct spinal problems. The manufacture of orthopedic implants such as joint replacement devices and spinal devices comprises a large sector of the orthopedic industry.

Because of the configuration of some orthopedic implants, various types of orthopedic implants need to be assembled before use. Sometimes assembly is accomplished before implantation and sometimes assembly is accomplished during implantation. In either case, the parts or components of the orthopedic implant need to be joined in a reliable, accurate and dependable manner that allows the assembly and retention of the components. Thus, a structure is necessary to allow the components of the orthopedic implant to be joined and retained in a reliable, accurate and dependable manner.

In view of the above, it is desirable to provide a structure to join and retain components or parts of an orthopedic implant in a reliable, accurate and dependable manner. It is thus an object of the present invention to provide a structure and/or manner to join one part of an orthopedic implant with another part of the orthopedic implant in order to hold the parts together during use.

SUMMARY OF THE INVENTION

An orthopedic implant structure is provided for joining and retaining components of a multi-part orthopedic device. The orthopedic implant joining and retaining structure may be embodied in two or more components of the multi-part orthopedic device.

In one form, the multi-part orthopedic implant joining and retaining structure is a resilient snap structure. The present structure provides a positive, reliable, accurate and dependable joining and retention mechanism that is fabricated from a bio-compatible material.

According to one embodiment, the retaining structure includes a partially open channel formed in one portion of one part of an orthopedic implant and a resilient flange formed in one portion of another part of the orthopedic implant. The channel has a cavity formed at a rear of the channel. A configured lip is formed on an end of the resilient flange. The resilient flange bends during insertion into the channel due to the configured lip and dimensions of the partially open channel. Once the lip of the flange reaches the cavity of the channel, the resiliency of the flange causes the flange to bend or snap into the cavity. Reverse motion of parts is inhibited by co-action of the lip and a front edge of the cavity.

Depending on the length of the cavity, the retaining structure may allow limited movement of one part relative to another part. In this manner, the orthopedic device may be limitedly dynamic.

According to another embodiment, the retaining structure includes resilient snap flanges formed on an interconnection component of the multi-part orthopedic implant. Corresponding recesses in another part of the multi-part orthopedic implant receives the interconnection component. Dimensioned channels terminating in an open area formed in two (or more) pieces of an orthopedic implant causes the deformation of the snap flanges of the interconnection component during connection that thereafter resiliently return to their original state upon reaching the open area.

Other snap configurations and orthopedic implants and/or devices are contemplated in accordance with the present principles. In one form, the resilient snap structure includes a resilient head structure of a bone screw that deforms upon insertion into a configured head structure of a spine fixation construct. In yet another form, the resilient snap structure includes configured, pivoting cams of a head structure of a spine fixation construct that snap into a configured connection plate. The connection plate is configured with a rim and trough that provide snap connection by the pivoting cams.

BRIEF DESCRIPTION OF THE DRAWINGS

The foregoing and other features of the present invention will become more apparent to one skilled in the art upon also reading the following description of embodiments with reference to the accompanying drawings wherein.

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION OF THE INVENTION

Figure 1:
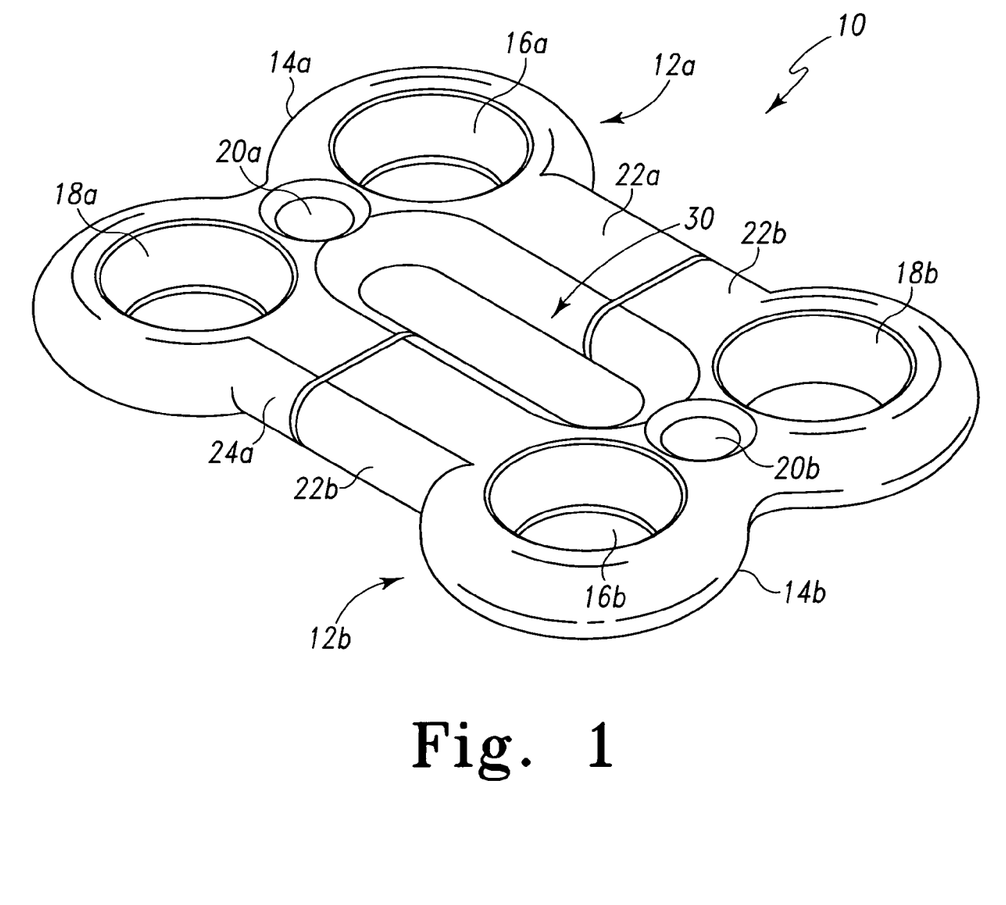
FIG. 1 is a perspective view of a one level (1-L), two piece spine plate utilizing an embodiment of a retaining structure in accordance with the present principles.

FIGS. 1-8 depict various views of an orthopedic implant or device utilizing an embodiment of the present invention and particularly utilizing a joining and retaining structure. Referring to FIG. 1 there is depicted an orthopedic implant generally designated 10 that is particularly a one level (1-L), two piece spine plate. The spine plate 10 is representative of the various types of spine plates that may use the present invention.

The spine plate 10 is preferably, but not necessarily, made from a suitable, biocompatible material such as titanium. The spine plate 10 is formed of identical first and second segments, parts, components or halves 12a and 12b one of which is rotated 180° relative to the other part, then joined with the other half. As such, the plate segment 12b is identical to plate segment 12a and thus the same parts of plate segment 12b are labeled with the same number but provided with the letter designation "b." It should be appreciated that the present invention is not dependent upon such symmetry and thus can be used on non-symmetrical segments of spine plates.

Figure 2:
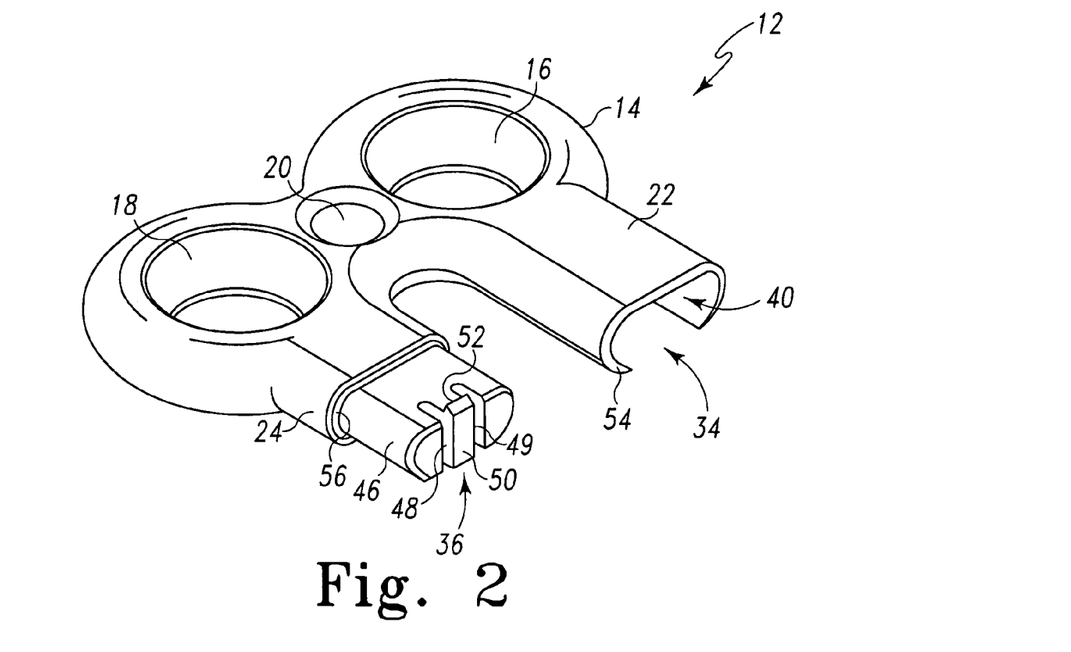
FIG. 2 is a top perspective view of the one segment of the one level, two piece spine plate of FIG. 1.
Figure 3:
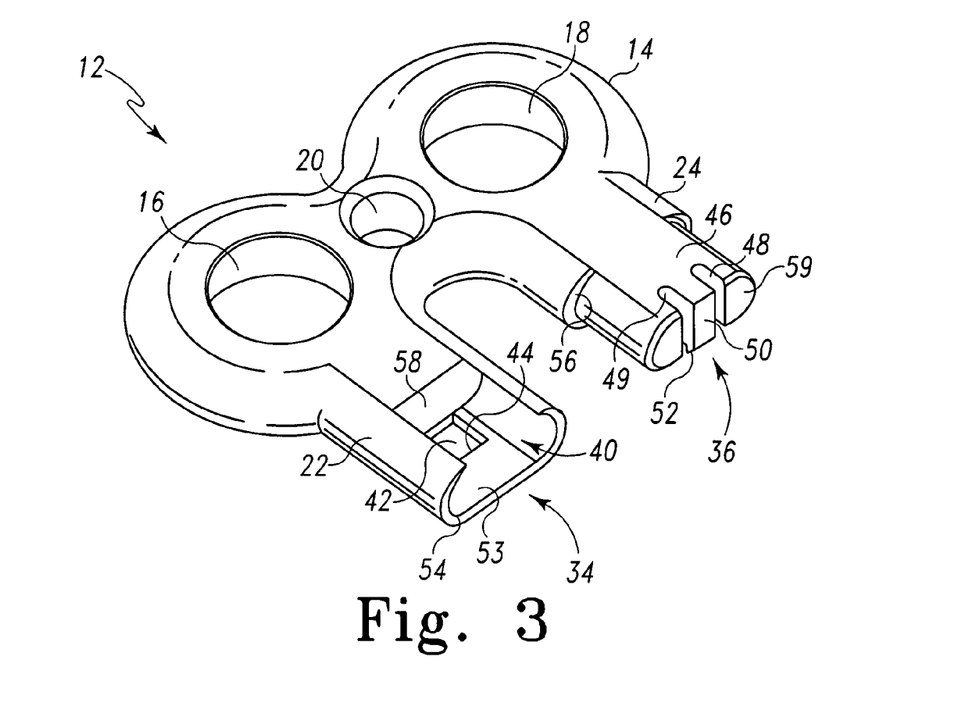
FIG. 3 is a bottom perspective view of the spine plate segment of FIG. 2.

Plate segment 12a has two screw bores 16a and 18a with a cover plate bore 20a disposed between the screw bores 16a and 18a. A first leg 22a extends from adjacent the screw bore 16a while a second leg 24a extends from adjacent the screw bore 18a. When joined, the plate segments 12a and 12b form an oblong opening or window 30. Referring additionally to FIGS. 2 and 3 (showing a top perspective view and a bottom perspective view respectively) a plate segment labeled 12 is shown representing the plate segments 12a and 12b since they are identical.

The leg 22 includes a reception area 34 defined by a partially open, configured slot or channel 40 that terminates in an end wall 58. The slot 40 includes a cutout, cavity, depression or concavity 42 having a front, sloping ledge 44. The leg 22 also defines a front surface 54.

The leg 24 includes a retention structure 36 on a front portion of a projection 46 extending beyond a stop surface 56. The retention structure 36 includes first and second relief slots 48 and 49 that define a flange 50. The flange 50 has a front lip 52 that extends upward from the surface of the flange 50 and thus the projection 46. The flange 50 is somewhat resilient in that pressure or force exerted onto the flange 50 through the lip 52 causes the flange 50 to deform or bend slightly in a direction of the applied pressure. Because the flange 50 is resilient, the flange 50 returns to its original position or normal state after the pressure or force upon the lip 52 ceases.

The flange 50 is adapted to be received in the cavity 42. With additional reference to FIGS. 4A and 4B, as the projection 46 is inserted into the slot 40, the sides of the slot 40 retain the projection 46 in the slot 40 while the flange 50 bends toward the open area of the slot 40 due to contact with surface 53 of the slot 40. Further travel of the flange 50 towards the end surface 58 of the slot 40 allows the lip 52 to encounter sloped ledge 44. Once the lip 52 encounters ledge 44, the resiliency of the flange 50 causes the flange to bend back (snap) into its original position and thus into the cavity 42.

Figure 4A:
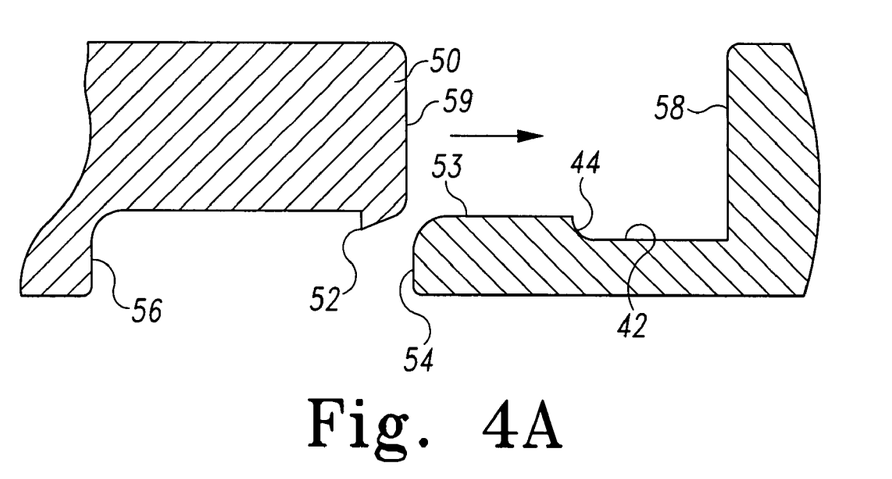
FIG. 4A is an enlarged sectional view of the retaining structure illustrating the manner in which the retaining structure joins.
Figure 4B:
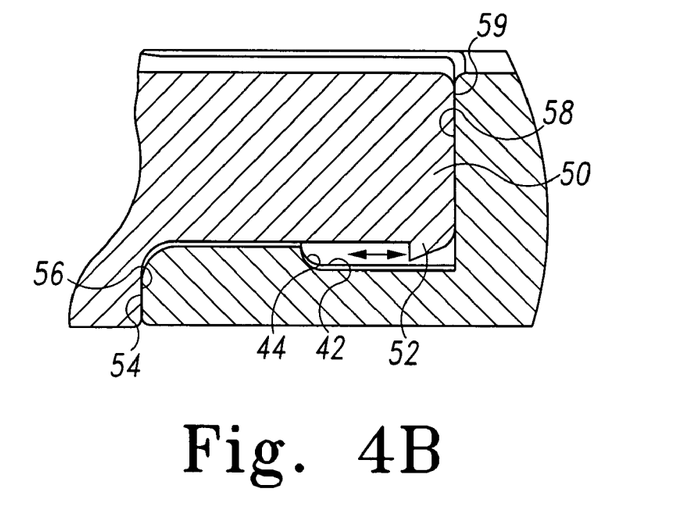
FIG. 4B is an enlarged sectional view of the retaining structure after joining.

Travel of two components relative to one another ceases when surface 59 contacts surface 58 and surface 56 contacts surface 54. As seen in FIG. 4B, the plate 10 may be limitedly dynamic to the extent that there is distance between the lip 52 and the ledge 44 as represented by the double-headed arrow. The plate 10 may be static if there is no distance between the lip 52 and the ledge 44.

Figure 5:
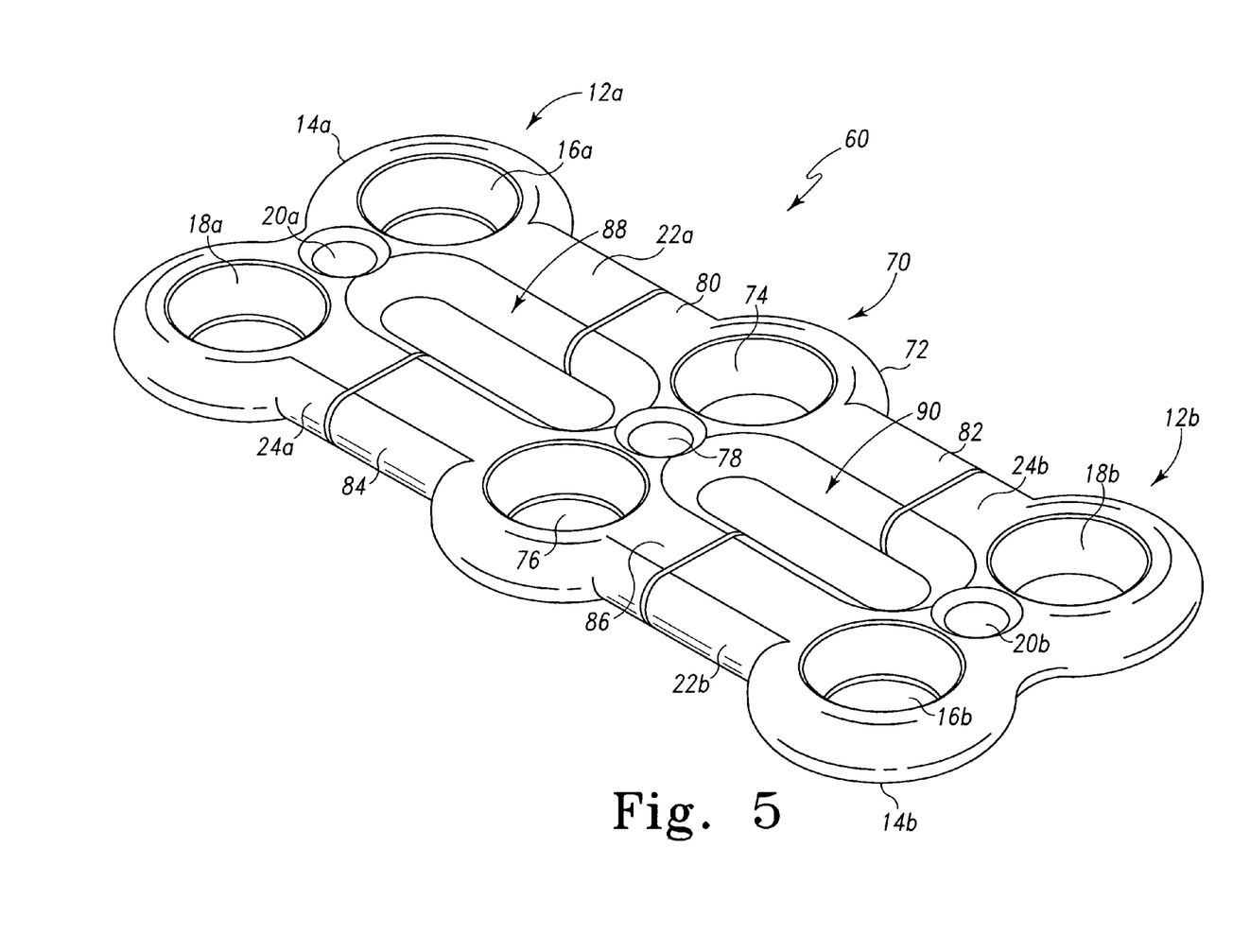
FIG. 5 is a perspective view of a two level (2-L), three piece spine plate utilizing an embodiment of a retaining structure in accordance with the present principles.

Referring to FIG. 5, there is depicted an embodiment of another orthopedic device generally designated 60 in which the present invention may be used. Particularly, FIG. 5 depicts a two level (2-L) spine plate. The two level spine plate is formed by providing a middle part or component 70 between the components 12a and 12b. The middle component 70 is configured to receive the end components 12a and 12b. The middle component 70 is formed of a body 72 having a first screw bore 74 and a second screw bore 76. A plate cover bore 78 is disposed between the screw bores 74 and 76. A first leg 80 extends from one side of the body 72 adjacent the bore 74. A second leg 82 extends from one side of the body 72 adjacent the bore 74 opposite to that of the first leg 80. A third leg 84 extends from one side of the body 72 adjacent the bore 76, while a fourth leg 86 extends from one side of the body 72 adjacent the bore 76 opposite to that of the third leg 84. The first and third legs 80, 84 extend in the same direction while the second and fourth legs 82, 86 extend in the same direction. The two level plate 60 thus defines first and second oblong windows 88 and 90. The window 88 is defined between the middle component 70 and the end component 12a while the window 90 is defined between the middle component 70 and the end component 12b.

Figure 6:
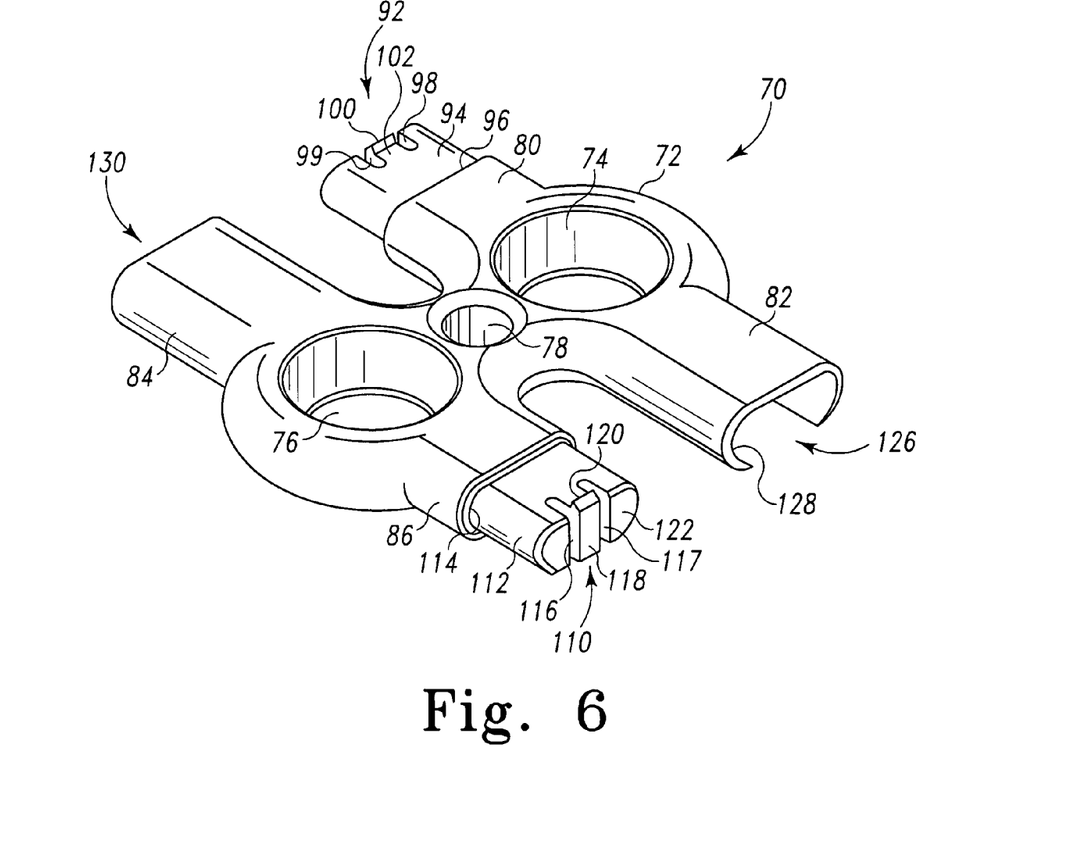
FIG. 6 is a top perspective view of a middle segment of the two level, three piece spine plate of FIG. 5.
Figure 7:
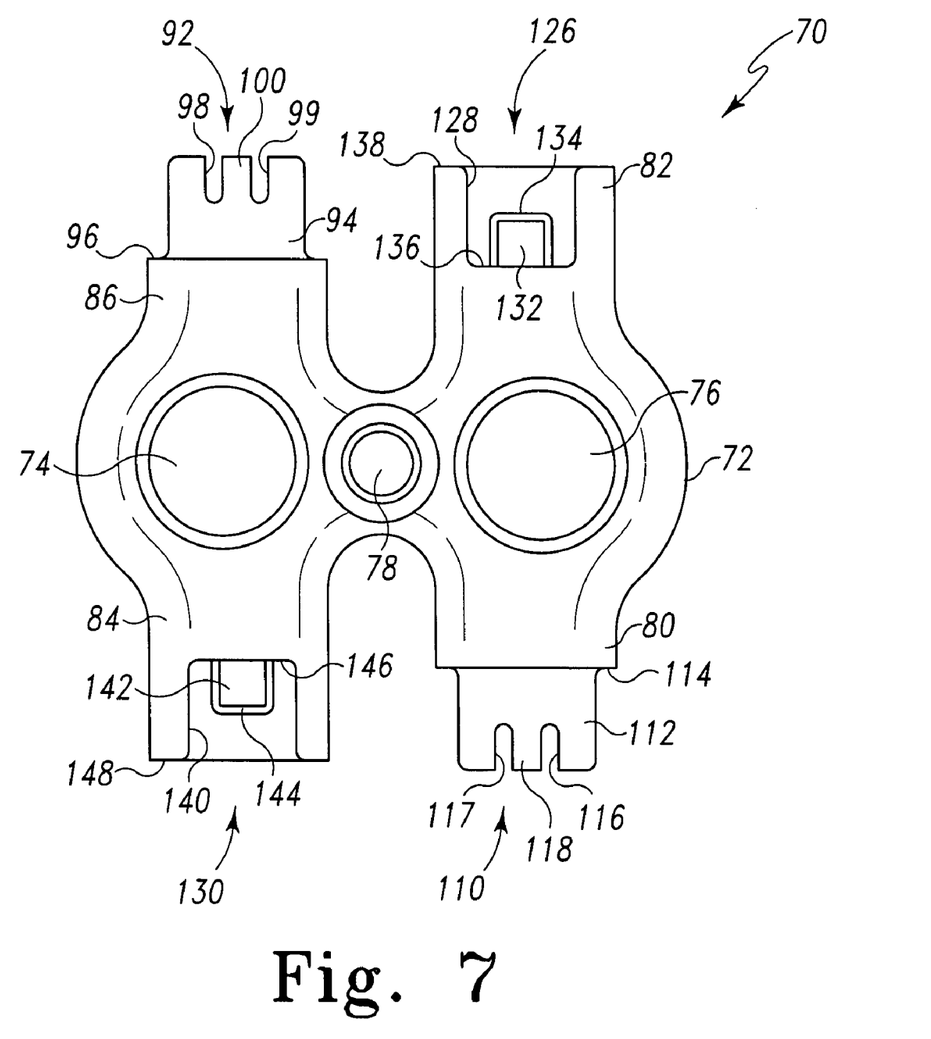
FIG. 7 is a bottom perspective view of the middle segment of FIG. 6.

Referring to FIGS. 6 and 7, there is depicted a top perspective view and a bottom plan view, respectively, of the middle component 72. The leg 80 includes a retention structure 92 on a front portion of a projection 94 extending beyond a stop surface 96. The retention structure 92 includes first and second relief slots 98 and 99 that define a flange 100. The flange 100 has a front lip 102 that extends upward from the surface of the flange 100 and thus the projection 96. The flange 100 is somewhat resilient in that pressure or force exerted onto the flange 100 through the lip 102 causes the flange 100 to deform or bend slightly in a direction of the applied pressure. Because the flange 100 is resilient, the flange 100 returns to its original position or normal state after the pressure or force upon the lip 102 ceases.

The leg 82 includes a reception area 126 defined by a partially open, configured slot or channel 128 that terminates in an end wall 136. The slot 128 includes a cutout 132 having a front, sloping ledge 134. The leg 82 also defines a front surface 138. The reception area 126 is configured to receive the retention structure 36b of the end component 12b in like manner to the reception of the retention structure 36b into the reception area 34a.

The leg 84 includes a reception area 130 defined by a partially open, configured slot or channel 140 that terminates in an end wall 146. The slot 140 includes a cutout 142 having a front, sloping ledge 144. The leg 84 also defines a front surface 148. The reception area 130 is configured to receive the retention structure 36a of the end component 12a in like manner to the reception of the retention structure 36a into the reception area 34b.

The leg 86 includes a retention structure 110 on a front portion of a projection 112 extending beyond a stop surface 114. The retention structure 110 includes first and second relief slots 116 and 117 that define a flange 118. The flange 118 has a front lip 120 that extends upward from the surface of the flange 118 and thus the projection 112. The flange 118 is somewhat resilient in that pressure or force exerted onto the flange 118 through the lip 120 causes the flange 118 to deform or bend slightly in a direction of the applied pressure. Because the flange 118 is resilient, the flange 118 returns to its original position or normal state after the pressure or force upon the lip 120 ceases.

Figure 8:
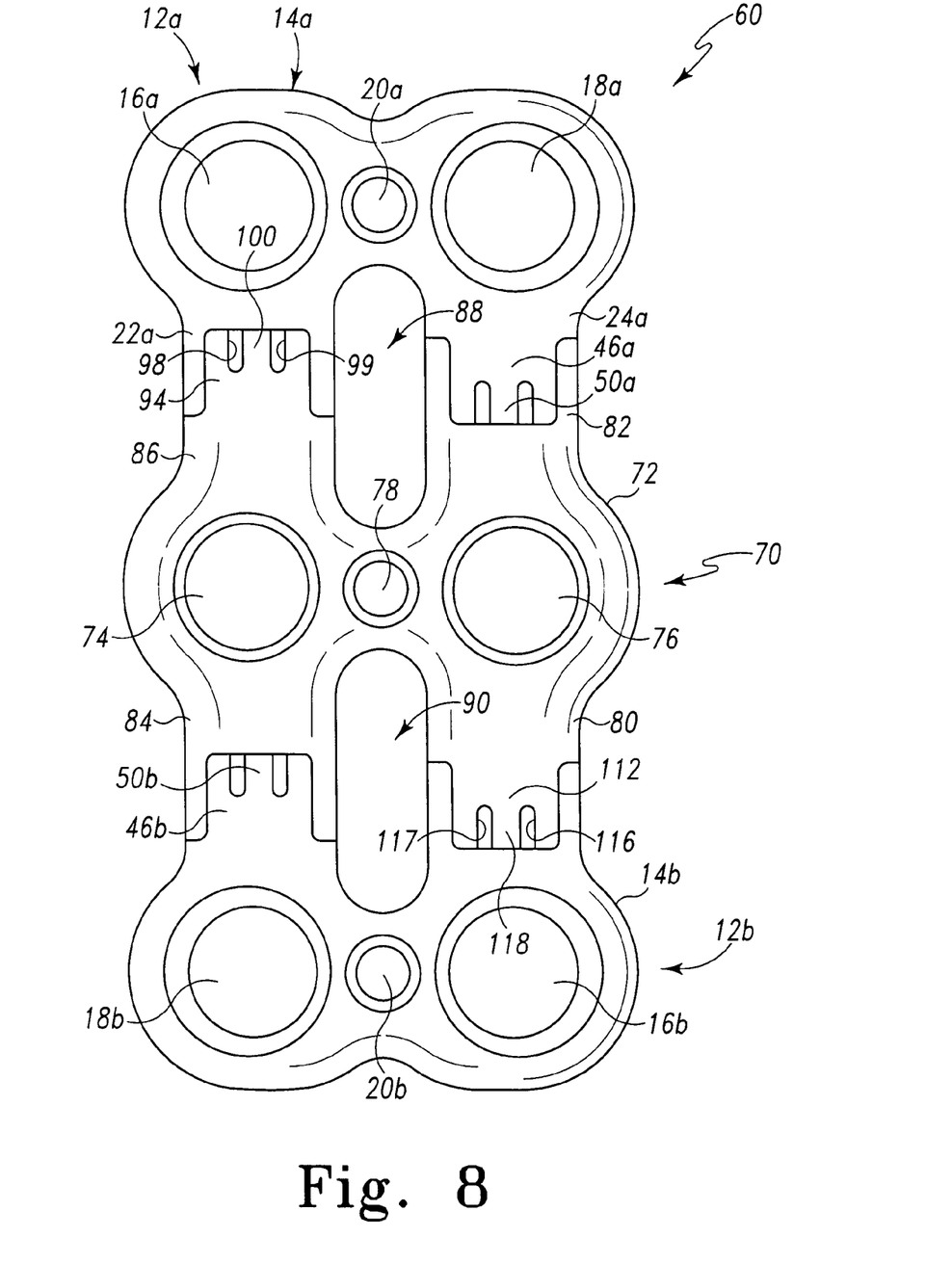
FIG. 8 is bottom plan view of the two level, three piece spine plate of FIG. 5.

It can be seen that the middle structure 70 is symmetric about a 180° rotation of itself. FIG. 8 depicts an underside view of the two level spine plate 60.

Figure 9:
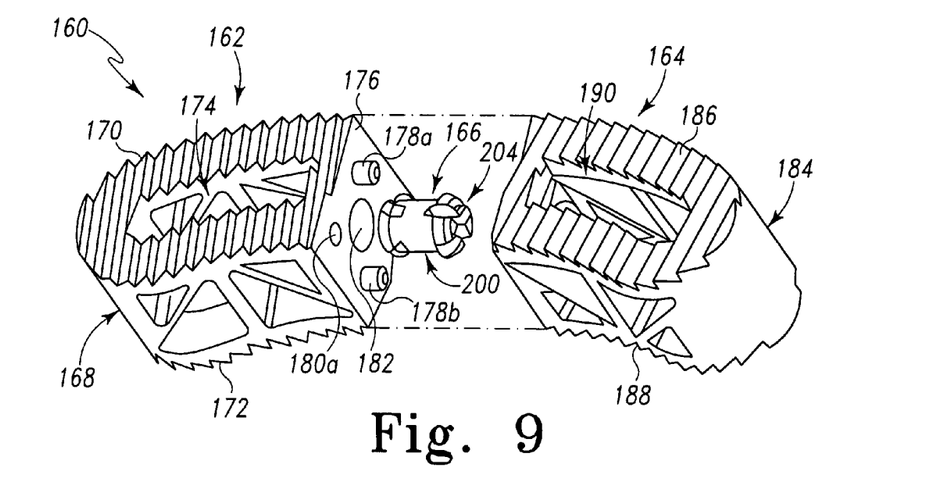
FIG. 9 is an exploded perspective view of a two-piece vertebral interbody device utilizing an embodiment of a retaining structure in accordance with the present principles.

FIGS. 9-14 depict various views of another orthopedic implant or device utilizing an embodiment of the present invention and particularly a joining and retaining structure. Referring to FIG. 9, there is depicted an orthopedic implant generally designated 160 that is particularly a two-piece, vertebral interbody or intrabody device. The two-piece, vertebral interbody device 160 is representative of the various types of N-piece vertebral interbody devices that may use the present invention. Particularly, pieces of the interbody device are connected to one another via a connection device having resilient snaps or snap structures. The resilient snaps deform when received by an interbody piece, but then return to their original position once received.

The interbody device 160 includes a first piece, portion or section 162 and a second piece, portion or section 164 that are joined by a connection device 166. The first and second pieces 162, 164 and the connection device 166 are formed of a bio-compatible material. Also, the nomenclature first and second is arbitrary.

The first piece 162 is defined by a generally arced oblong body 168. The body 168 has a toothed or serrated upper surface 170 and a toothed or serrated lower surface 172. The nomenclature upper and lower is arbitrary. The body 168 defines an inner cavity 174 and a plurality of side windows. While one end of the body 168 is curved, the other end has an essentially flat face 176. Anti-rotation features are provided on/in the flat face 176. Particularly, first and second posts or pegs 178a, 178b are provided on opposite corners of the face 176. Additionally, first and second bores 180a, 180b are provided on opposite corners, opposite to the posts 178a, 178b. A central connection device bore 182 is also provided in the face 176.

The second piece 164 is defined by a generally arced oblong body 184. The body 184 has a toothed or serrated upper surface 186 and a toothed or serrated lower surface 188. The nomenclature upper and lower is arbitrary. The body 184 defines an inner cavity 190 and a plurality of side windows. While one end of the body 184 is curved, the other end has an essentially flat face 192 (see, e.g. FIG. 10). Anti-rotation features are provided on/in the face 192. Particularly, first and second posts or pegs 194a, 194b are provided on opposite corners of the face 192. Additionally, first and second bores 196a, 196b are provided on opposite corners, opposite to the posts 194a, 194b. A central connection device bore 198 is also provided in the face 192.

Figure 10:
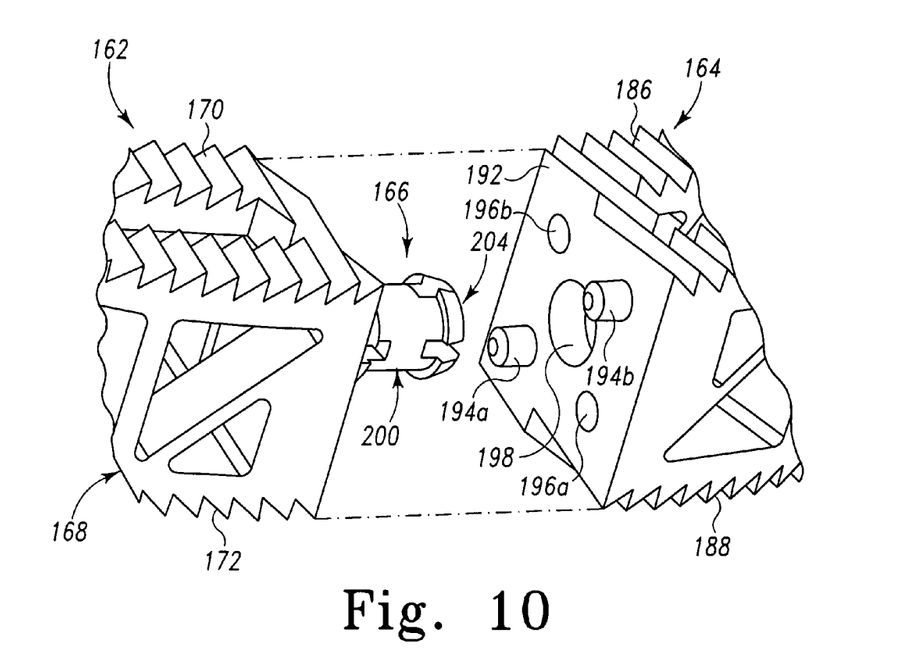
FIG. 10 is an enlarged, perspective view of a portion of the two-piece vertebral interbody device illustrating anti-rotation features thereof.

The posts 178a, 178b of the body 168 of the first piece 160 are sized and configured to be received in the bores 196b, 196a, respectively, in the face 192 of the body 184 of the second piece 162 when joined. Likewise, the posts 194a, 194b of the body 184 of the second piece 162 are sized and configured to be received in the bores 180b, 180a, respectively, in the face 176 of the body 168 of the first piece 160 when joined. The reception of posts and bores upon joining of the first and second pieces 160, 162 prohibits rotation of one piece relative to another piece (anti-rotation).

Figure 11:
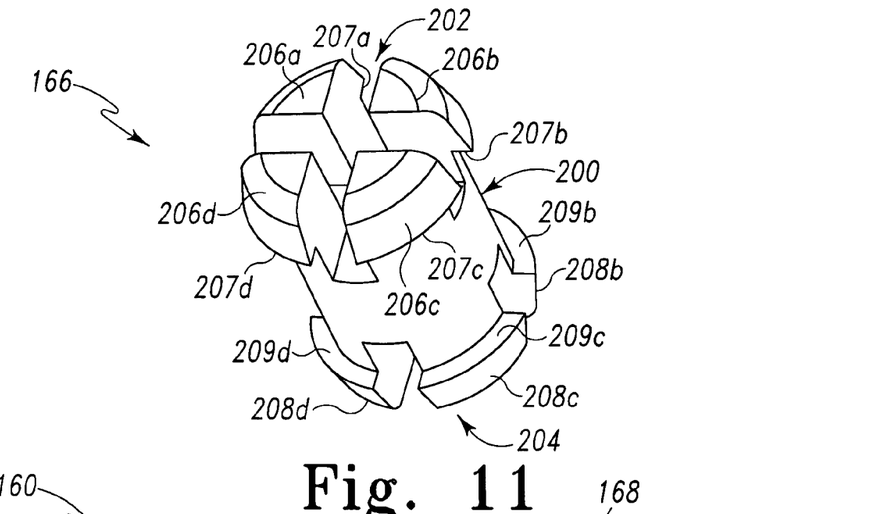
FIG. 11 is an enlarged perspective view of a two-sided retention post utilized to join the two pieces of the vertebral interbody device of FIG. 9.
Figure 12:
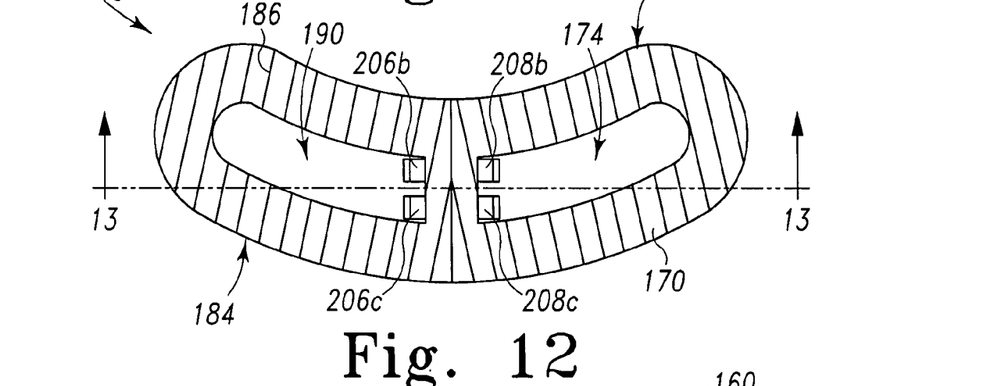
FIG. 12 is a top view of the two-piece vertebral interbody device of FIG. 9, assembled.

FIG. 11 particularly depicts the connection device 166 that allows the joining of the first and second pieces 162, 164. The connection device 166 is defined by a generally cylindrical body 200 having a first head or end 202 and a second head or end 204. The nomenclature first and second is arbitrary. The first and second heads 202, 204 are formed as resilient snap structures. The first head 202 has four snaps 206a, 206b, 206c, 206d that define an "X" pattern of slots in the first head 202 and respective ledges 207a, 207b, 207c, 207d. The second head 204 has four snaps 208a, 208b, 208c, 208d that define an "X" pattern of slots in the first head 204 and respective ledges 209a, 209b, 209c, 209d. A portion of each of the snaps 206a, 206b, 206c, 206d, 208a, 208b, 208c, 208d extend radially beyond the radial dimension of the cylindrical body 200 such that the ledges 207a, 207b, 207c, 207d, 209a, 209b, 209c, 209d of the respective snaps 206a, 206b, 206c, 206d, 208a, 208b, 208c, 208d extend radially beyond the radial dimension of the cylindrical body 200 (i.e. the middle portion thereof between the heads 202, 204).

Figure 13:
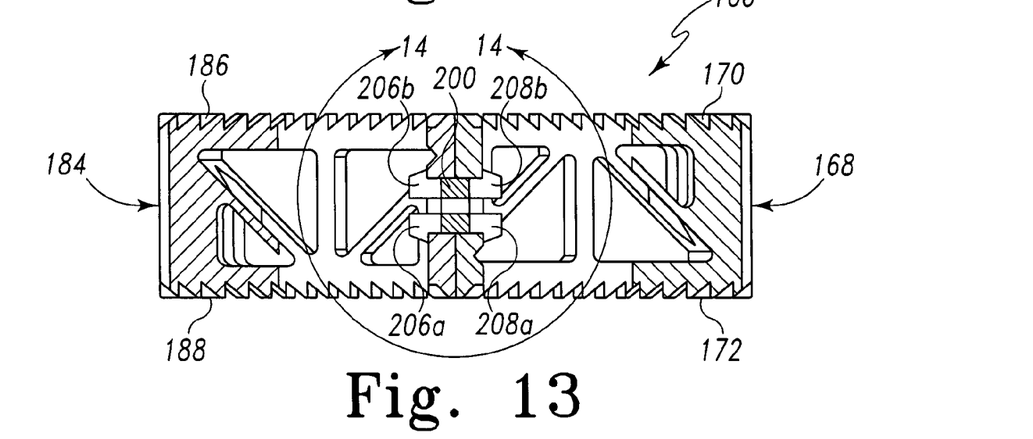
FIG. 13 is a sectional view of the two-piece vertebral interbody device taken along line 13-13 of FIG. 12.
Figure 14:
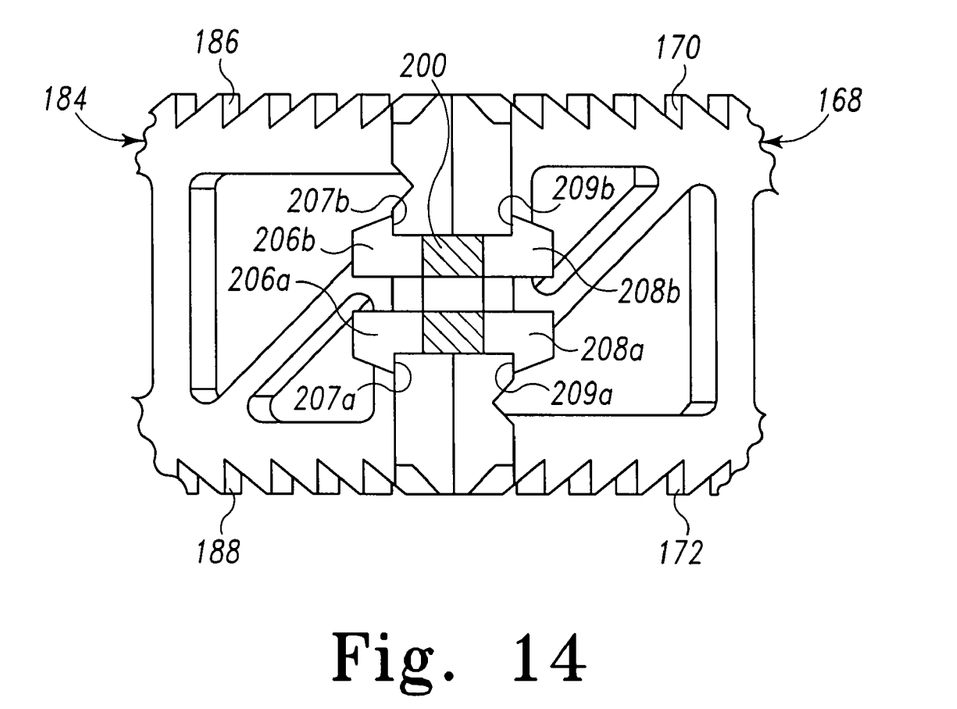
FIG. 14 is an enlarged sectional view of a portion of the two-piece vertebral interbody device taken along circle 14-14 of FIG. 13.

With particular reference to FIGS. 13 and 14, the central bore 182 of the first piece 160 and the central bore 198 of the second piece 162 is sized radially to receive the connection device 200. Particularly, the radial size (diameter) of each central bore 182, 198 is sized to cause the snaps 206a, 206b, 206c, 206d, 208a, 208b, 208c, 208d to deform radially inward during insertion and travel through the bores 182, 198 but snugly surround the middle cylindrical portion of the body 200 of the connection device 166. The length of each of the central bores 182 and 198 is such that the snaps 206a, 206b, 206c, 206d, 208a, 208b, 208c, 208d will spring or return back to their original position and allow the ledges 207a, 207b, 207c, 207d, 209a, 209b, 209c, 209d of respective snaps 206a, 206b, 206c, 206d, 208a, 208b, 208c, 208d to rest against the inner walls of the respective pieces 160, 162. In this manner, the two pieces 160, 162 of the interbody device are joined, coupled, or connected.

Other orthopedic implants may utilize embodiments of the present invention. For example, spine fixation constructs may utilize the present joining and retaining structure. In one form, a bone screw structure is connected to a rod holder of a rod holder construct via a resilient snap structure. The resilient snap structure of the rod holder expands when a configured head of the bone screw structure is inserted therein and then contracts back to its normal state around the configured head to retain the configured head and thus the bone screw structure. In this embodiment, the spine fixation construct thus includes a bone screw structure and a rod holder construct. A spine rod is retained in and by the rod holder construct and may or may not be considered as part of the spine fixation construct.

Another form of a spine fixation construct that utilizes the present joining and retaining structure provides for two bone screw structures, a snap connection plate and two head constructs form. In this embodiment, the two head constructs are coupled to the snap connection plate via cam lock snaps. A construct comprising two head constructs and the snap connection plate is then situated onto the two bone screw structures.

While the invention has been illustrated and described in detail in the drawings and foregoing description, the same is to be considered as illustrative and not restrictive in character, it being understood that only preferred embodiments has been shown and described and that all changes and modifications that come within the spirit of the invention are desired to be protected.

What is claimed is:

1. An orthopedic implant comprising:
a first component comprising:
   a first leg having a projection and a lip extending from the projection;
   a second leg spaced apart and generally parallel with the first leg, the second leg having a channel defined by an end surface, a pair of side walls, and an intermediate wall extending between the pair of side walls, the intermediate wall having a cavity at least partially defined by a ledge which is spaced apart from the end surface;
a second component for assembly with the first component, the second component comprising:
   a first leg having a projection and a lip extending from the projection;
   a second leg spaced apart and generally parallel with the first leg, the second leg having a channel defined by an end surface, a pair of side walls, and an intermediate wall extending between the pair of side walls, the intermediate wall having a cavity at least partially defined by a ledge which is spaced apart from the end surface;
wherein the channel on the second leg of the second component receives the projection on the first leg of the first component so that the lip on the first leg of the first component engages the ledge on the second leg of the second component in a snap-fit engagement, and wherein the channel on the second leg of the first component receives the projection on the first leg of the second component so that the ledge on the second leg of the first component engages the lip on the first leg of the second component in a snap-fit engagement;
wherein limited movement of the first component relative to the second component after the snap-fit engagement is allowed due to spacing between the lip on the projections and the ledges of the cavities.

2. The orthopedic implant of claim 1, wherein the first component comprises one portion of a spine plate and the second component comprises another portion of the spine plate.

3. The orthopedic implant of claim 1, wherein the projections each have an end surface configured to engage the end surface of the channels to limit movement of the first component relative to the second component.

4. The orthopedic implant of claim 3, wherein the the first leg of the projection on the first component comprises a resilient flange, and the first leg of the projection on the second component comprises a resilient flange.

5. The orthopedic implant of claim 4, wherein the cavity on the second leg of the first component is formed at a rear of its channel, and the cavity on the first leg of the second component is formed at a rear of its channel.

6. The orthopedic implant of claim 5, wherein the channels on the first component and the second component each comprises a partially open channel.

7. The orthopedic implant of claim 5, wherein the lip on the first leg of the first component is formed as a resilient flange on the, projection wherein the lip on the first leg of the second component is formed as a resilient flange on the projection; and wherein the resilient flanges are compressed during insertion into the channels due to the lips and dimensions of the partially open channels and then decompresses once the lips of the flanges reach the cavities of the channels and the resiliency of the flanges causes the flanges to snap into the cavities.

8. The orthopedic implant of claim 7, wherein each cavity includes a ridge and front edge that inhibits reverse motion of the first and second components.

9. The orthopedic implant of claim 1, wherein the assembled first component and the second component provide an oblong window between the spaced apart first legs and second legs.

10. The orthopedic implant of claim 1, wherein each of the sidewalls has an in-turned edge.

11. An orthopedic implant comprising:
a first component comprising:
   a first leg having a projection with a pair of relief slots defining a resilient flange integrally formed with the first leg, and a lip extending from the flange;
   a second leg spaced apart and generally parallel with the first leg, the second leg having a channel and a cavity formed in a planer surface of the channel and defined at least partially by a ledge;
a second component for assembly with the first component, the second component comprising:
   a first leg having a projection with a pair of relief slots defining a resilient flange integrally formed with the first leg, and a lip extending from the flange;
   a second leg spaced apart and generally parallel with the first leg, the second leg having a channel and a cavity formed in a planer surface of the channel and defined at least partially by a ledge;
wherein the channel on the second leg of the second component receives the projection on the first leg of the first component so that lip on the resilient flange on the first leg of the first component couples to the aperture formed in the channel of the second component in a snap-fit engagement between the lip and the ledge;
wherein the channel on the second leg of the first component receives the projection on the first leg of the second component so that the resilient flange on the second leg of the first component couples to the aperture formed in the channel on the first leg of the second component by in a snap-fit engagement between the lip and the ledge during assembly of the first and second components whereby the first and second components are joined and retained together;
wherein limited movement of the first component relative to the second component after the snap-fit engagement is allowed due to spacing between the lip on the projections and the ledges of the cavities.

12. The orthopedic implant of claim 11, wherein the ledge is an edge structure that engages a lip on the resilient flange.

13. The orthopedic implant of claim 12, wherein the cavity is formed by a bore.

14. The orthopedic implant of claim 11, wherein the assembled first component and the second component provide an oblong window between the spaced apart first legs and second legs.

15. The orthopedic implant of claim 11, wherein each of the sidewalls has an in-turned edge.

* * * * *